US00PP18822P2

(12) United States Plant Patent
Kientzler

(10) Patent No.: US PP18,822 P2
(45) Date of Patent: May 20, 2008

(54) **NEW GUINEA *IMPATIENS* PLANT NAMED 'KIORONA'**

(50) Latin Name: *Impatiens hawkeri*
Varietal Denomination: Kiorona

(75) Inventor: Ludwig Kientzler, Gensingen (DE)

(73) Assignee: The Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/518,582

(22) Filed: Sep. 8, 2006

(51) Int. Cl.
*A01H 5/00* (2006.01)

(52) U.S. Cl. ..... Plt./318
(58) Field of Classification Search ..... Plt./318
See application file for complete search history.

(56) References Cited

PUBLICATIONS

Upovrom Plant Variety Database GTITM 2007/02, GTI Jouve Retrieval Software, Citation for *Impatiens* 'Kiorona', one page.*

Royalty Administration International [online], [retrieved on Aug. 15, 2007]. Retrieved from the Internet <http://www.rai–worldwide.com/> 2 pages.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of New Guinea *Impatiens* plant named 'Kiorona', characterized by its compact, upright, outwardly spreading and mounded plant habit; freely branching habit; dense and bushy growth habit; dark green-colored leaves; freely flowering habit; and large dark red-colored flowers that are positioned above and beyond the foliage.

1 Drawing Sheet

Botanical designation: *Impatiens hawkeri.*
Cultivar denomination: 'Kiorona'.

BACKGROUND OF THE INVENTION

The present invention relates to a new and distinct cultivar of New Guinea *Impatiens* plant, botanically known as *Impatiens hawkeri,* and hereinafter referred to by the name 'Kiorona'.

The new *Impatiens* is a product of a planned breeding program conducted by the Inventor in Gensingen, Germany. The objective of the breeding program was to develop new *Impatiens* cultivars with numerous large flowers and attractive foliage and flower coloration.

The new *Impatiens* originated from a cross-pollination made by the Inventor of two unnamed proprietary selections of *Impatiens hawkeri,* not patented. The cultivar Kiorona was discovered and selected by the Inventor as a flowering plant within the progeny of the stated cross-pollination in a controlled environment in Gensingen, Germany.

Asexual reproduction of the new cultivar by terminal cuttings propagated in a controlled environment in Gensingen, Germany has shown that the unique features of this new *Impatiens* are stable and reproduced true to type in successive generations of asexual reproduction.

SUMMARY OF THE INVENTION

The cultivar Kiorona has not been observed under all possible environmental conditions. The phenotype may vary somewhat with variations in environment such as temperature and light intensity, without, however, any variance in genotype.

The following traits have been repeatedly observed and are determined to be the unique characteristics of 'Kiorona'.

These characteristics in combination distinguish 'Kiorona' as a new and distinct cultivar of New Guinea *Impatiens:*

1. Compact, upright, outwardly spreading and mounded plant habit.
2. Freely branching habit; dense and bushy growth habit.
3. Dark green-colored leaves.
4. Freely flowering habit.
5. Large dark red-colored flowers that are positioned above and beyond the foliage.

In side-by-side comparisons conducted in Gensingen, Germany, plants of the new *Impatiens* differed from plants of the parent selections primarily in plant size and flower color.

Plants of the new *Impatiens* can be compared to plants of the New Guinea *Impatiens* cultivar Kimptamp, not patented. In side-by-side comparisons conducted in Gensingen, Germany, plants of the new *Impatiens* differed from plants of the cultivar Kimptamp primarily in flower color as plants of the cultivar Kimptamp had flowers with more orange tones than plants of the new *Impatiens.*

BRIEF DESCRIPTION OF THE PHOTOGRAPHS

The accompanying photographs illustrate the overall appearance of the new *Impatiens.* The photographs show the colors as true as it is reasonably possible to obtain in colored reproductions of this type. Colors in the photographs may differ slightly from the color values cited in the detailed botanical description which accurately describe the colors of the new *Impatiens.*

The photograph at the bottom of the sheet comprises a side perspective view of a typical flowering plant of 'Kiorona' grown in a container.

The photograph at the top of the sheet is a close-up view of typical flowers of 'Kiorona'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Encinitas, Calif. during the winter and early spring in a polyethylene-covered greenhouse and under conditions and practices which approximate those generally used in commercial New Guiena *Impatiens* production. During the production of the plants, day temperatures averaged 24° C., night temperatures averaged 19° C. and light levels averaged 4,000 foot candles. Measurements and numerical values represent averages for typical flowering plants. Single plants were grown in one-gallon containers and were about 18 weeks old when the photographs and the detailed description were taken.

Botanical classification: *Impatiens hawkeri* cultivar Kiorona.

Parentage:

*Female, or seed, parent.*—Unnamed proprietary selection of *Impatiens hawkeri,* not patented.

*Male, or pollen parent.*—Unnamed proprietary selection of *Impatiens hawkeri,* not patented.

Propagation:

*Type.*—Vegetative cuttings.

*Time to initiate roots, summer.*—About 14 days at 23° C.

*Time to initiate roots, winter.*—About 17 days at 20° C.

*Time to produce a rooted young plant, summer.*—About 21 days at 23° C.

*Time to produce a rooted young plant, winter.*—About 24 days at 20° C.

*Root description.*—Fine, fibrous; white (close to 155D) to brown (close to 163A) in color.

*Rooting habit.*—Freely branching.

Plant description:

*Plant form.*—Compact, upright, outwardly spreading and mounded plant habit.

*Growth and branching habit.*—Vigorous and freely branching habit; about ten lateral branches developing at the base; dense and bushy growth habit. Pinching, that is, removal of the terminal apices, is typically not required, but will enhance branching.

*Plant height.*—About 18 cm.

*Plant diameter or spread.*—About 33 cm.

*Lateral branches.*—Length: About 13 cm. Diameter: About 9 mm. Internode length: About 3.5 cm to 4 cm. Texture: Smooth, glabrous. Color: Darker than 183A.

Foliage description:

*Arrangement.*—Opposite or in whorls, simple.

*Length.*—About 9 cm.

*Width.*—About 3.7 cm.

*Shape.*—Elliptical.

*Apex.*—Acuminate.

*Base.*—Attenuate.

*Margin.*—Serrate with ciliation.

*Texture, upper and lower surfaces.*—Smooth, glabrous.

*Venation pattern.*—Pinnate.

*Color.*—Developing foliage, upper surface: 147A. Developing foliage, lower surface: 147B. Fully expanded foliage, upper surface: Darker than 147A; venation, 147C. Fully expanded foliage, lower surface: 147B; venation, 185A.

*Petiole.*—Length: About 2.2 cm. Diameter: About 3 mm. Texture, upper and lower surfaces: Smooth, glabrous. Color, upper and lower surfaces: 183B.

Flower description:

*Flower type and flowering habit.*—Single axillary flowers. Freely flowering habit; usually about seven to eight open flowers and flower buds per lateral branch. Flowers positioned above the foliage and typically face upright or outward. Flowers last about one week under greenhouse conditions. Petals self-cleaning, gynoecium persistent. Flowers not fragrant.

*Natural flowering season.*—Year-round under greenhouse conditions. In the garden, flowering from spring until fall in Germany. Plants begin flowering about eight to twelve weeks after planting.

*Flower size.*—Length: About 6.5 cm. Width: About 6.4 cm. Depth: About 1.5 cm.

*Flower buds.*—Length: About 2.5 cm. Diameter: About 1.2 cm. Shape: Ovoid; pointed. Color: 46A.

*Petals.*—Quantity/arrangement: Five per flower in a single whorl. Length, banner petal: About 3.2 cm. Length, lateral petals: About 3.3 cm. Length, lower petals: About 3.7 cm. Width, banner petal: About 4.8 cm. Width, lateral and lower petals: About 4.2 cm. Shape: Cordate. Apex: Emarginate. Base: Acute. Margin: Entire. Texture, upper and lower surfaces: Smooth, glabrous. Color: When opening and fully opened, upper surface: 46A; towards the base, 46B. When opening and fully opened, lower surface: 46B.

*Sepals.*—Quantity/arrangement: Three; one modified into an elongated spur. Length: About 1.4 cm. Width: About 8 mm. Shape: Elliptical. Apex: Acuminate. Base: Obtuse. Margin: Entire. Texture, upper and lower surfaces: Smooth, glabrous. Color, upper surface: 185B. Color, lower surface: 185D. Spur length: About 5.5 cm. Spur diameter: At flower, about 4 mm; at apex, less than 1 mm. Spur texture: Smooth, glabrous. Spur color: 59A to 59B.

*Peduncles.*—Length: About 6.2 cm. Diameter: About 2.5 mm. Angle: About 30° from vertical. Strength: Strong. Texture: Smooth, glabrous. Color: 59A.

*Reproductive organs.*—Stamens: Quantity: Five fused at anthers; filaments free. Anther size: About 4 mm by 7 mm. Anther color: 10B. Pollen amount: Moderate. Pollen color: 11D. Pistils: Quantity per flower: One. Pistil length: About 6 mm. Stigma shape: Rounded. Stigma color: 145D. Style color: 144A. Ovary color: 144A.

*Seed/fruit.*—Seed and fruit production have not been observed.

Disease/pest resistance: Plants of the new *Impatiens* have not been observed to be resistant to pathogens and pests common to New Guinea *Impatiens*.

Temperature tolerance: Plants of the new *Impatiens* have been observed to tolerate temperatures from about 16° C. to about 30° C.

It is claimed:

1. A new and distinct New Guinea *Impatiens* plant named 'Kiorona' as illustrated and described.

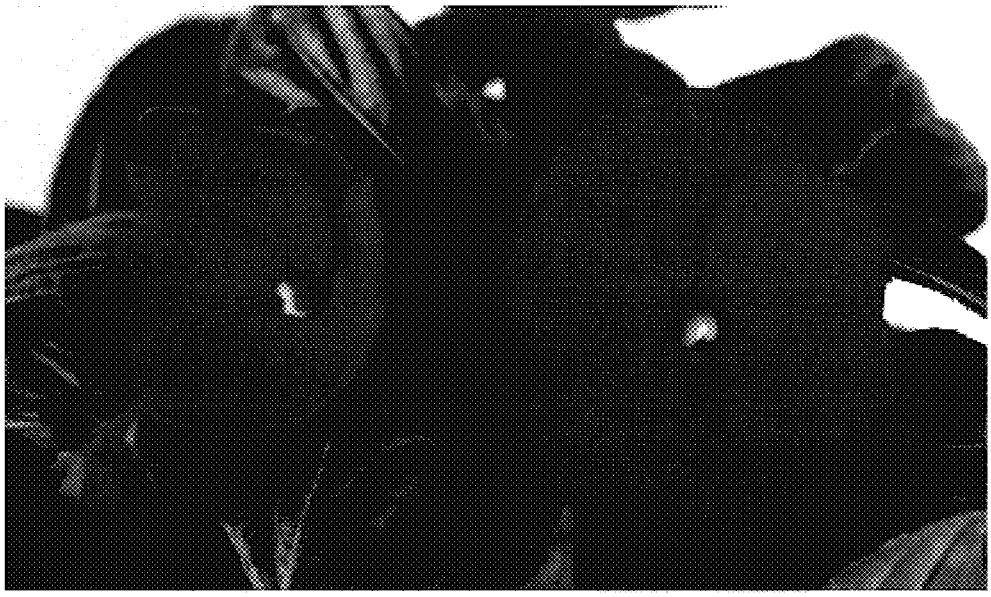
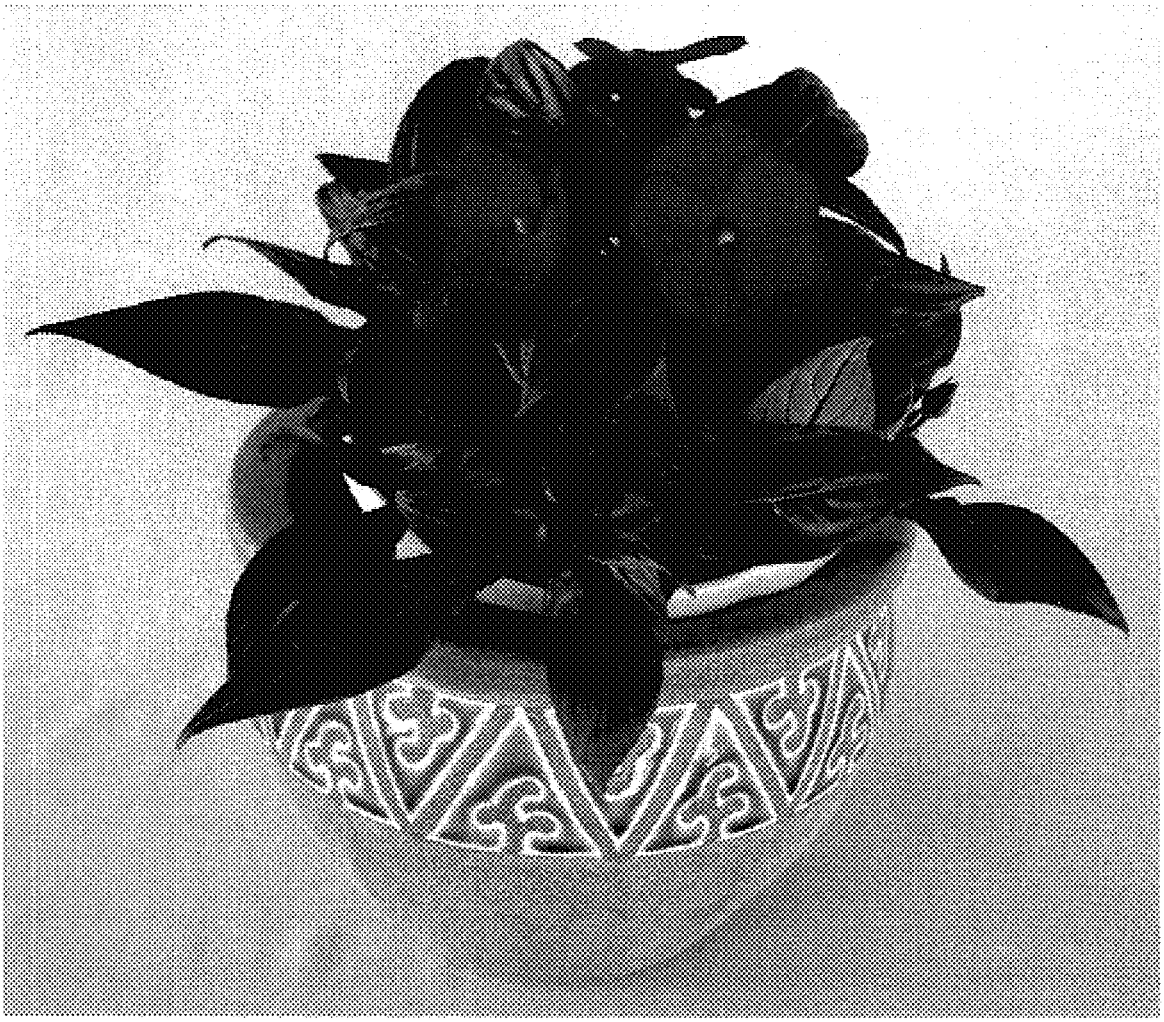

* * * * *